US011167118B1

(12) United States Patent
Le Roux et al.

(10) Patent No.: US 11,167,118 B1
(45) Date of Patent: Nov. 9, 2021

(54) SUNBLOCK LOTION SPRAY BOOTH

(71) Applicants: Marthinus Le Roux, Cooper City, FL (US); Marysia Le Roux, Cooper City, FL (US)

(72) Inventors: Marthinus Le Roux, Cooper City, FL (US); Marysia Le Roux, Cooper City, FL (US)

( * ) Notice: Subject to any disclaimer, the term of this patent is extended or adjusted under 35 U.S.C. 154(b) by 399 days.

(21) Appl. No.: 16/385,039

(22) Filed: Apr. 16, 2019

(51) Int. Cl.
*A61M 35/00* (2006.01)
*B05B 16/40* (2018.01)
*B05B 16/60* (2018.01)
*G07F 13/00* (2006.01)

(52) U.S. Cl.
CPC ............. *A61M 35/25* (2019.05); *B05B 16/40* (2018.02); *B05B 16/60* (2018.02); *G07F 13/00* (2013.01)

(58) Field of Classification Search
CPC ........ A61M 35/25; B05B 16/40; B05B 16/60; G07F 13/00
USPC ............................................... 118/300; 4/615
See application file for complete search history.

(56) References Cited

U.S. PATENT DOCUMENTS

| | | | |
|---|---|---|---|
| 5,460,192 A | 10/1995 | McClain | |
| 6,302,122 B1 | 10/2001 | Parker | |
| 6,554,208 B1 | 4/2003 | Venuto, Sr. | |
| 6,918,897 B2 | 7/2005 | Severino | |
| D618,360 S | 6/2010 | Mac | |
| 8,545,461 B2 | 10/2013 | Thomason | |
| 9,579,681 B2 | 2/2017 | Lotterhos | |
| 2002/0112738 A1* | 8/2002 | Parker | A61M 35/25 132/333 |
| 2004/0232257 A1* | 11/2004 | Venuto, Sr. | A45D 44/00 239/200 |
| 2005/0184016 A1* | 8/2005 | Silverman | B05B 16/00 211/87.01 |
| 2006/0231567 A1 | 10/2006 | Perrone | |
| 2007/0107121 A1* | 5/2007 | Smith | B05B 16/60 4/615 |
| 2007/0125798 A1 | 6/2007 | McGuire | |
| 2007/0197982 A1* | 8/2007 | Thomason | A61M 35/25 222/2 |
| 2009/0157015 A1* | 6/2009 | Lotterhos | G07F 13/00 604/289 |

(Continued)

FOREIGN PATENT DOCUMENTS

WO 2007064886 6/2007

*Primary Examiner* — Andrew J Mensh
*Assistant Examiner* — Nhu Q. Tran
(74) *Attorney, Agent, or Firm* — Kyle A. Fletcher, Esq.

(57) ABSTRACT

In embodiments, the sunblock lotion spray booth comprises a booth, a plurality of spray columns, a plurality of canisters, a pump, a ventilator, and one or more payment receiving devices. The booth may be adapted to spray one or more tanning products onto a user via the plurality of spray columns located within the booth once a payment receiving device and an activation button have been activated. As non-limiting examples, the one or more tanning products may be sunblock lotions having different SPF values, bronzers, or combinations thereof. One or more of the plurality of spray columns may be height-adjustable. The pump may move the tanning products from the plurality of canisters to a plurality of nozzles located on the spray columns via tubing within the walls of the booth. The ventilator may circulate air within the booth.

18 Claims, 5 Drawing Sheets

(56) References Cited

U.S. PATENT DOCUMENTS

| | | | |
|---|---|---|---|
| 2010/0001097 A1* | 1/2010 | Spivak | B05B 14/40 239/207 |
| 2013/0269112 A1* | 10/2013 | Legare | A47G 27/0231 5/648 |
| 2020/0224432 A1* | 7/2020 | Meyers | E04F 15/02194 |

* cited by examiner

SUNBLOCK LOTION SPRAY BOOTH

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of sun protection, more specifically, a sunblock lotion spray booth.

SUMMARY OF INVENTION

In embodiments, the sunblock lotion spray booth comprises a booth, a plurality of spray columns, a plurality of canisters, a pump, a ventilator, and one or more payment receiving devices. The booth may be adapted to spray one or more tanning products onto a user via the plurality of spray columns located within the booth once a payment receiving device and an activation button have been activated. As non-limiting examples, the one or more tanning products may be sunblock lotions having different SPF values, bronzers, or combinations thereof. One or more of the plurality of spray columns may be height-adjustable. The pump may move the tanning products from the plurality of canisters to a plurality of nozzles located on the spray columns via tubing within the walls of the booth. The ventilator may circulate air within the booth.

An object of the invention is to apply one or more tanning products to a user by pumping the products from a plurality of canisters via a plurality of nozzles located within a booth.

Another object of the invention is to provide height adjusters for the plurality of nozzles.

A further object of the invention is to provide a ventilator on the roof of the booth.

Yet another object of the invention is to provide one or more payment receiving devices and an activation button to start the dispensing of the tanning products.

These together with additional objects, features and advantages of the sunblock lotion spray booth will be readily apparent to those of ordinary skill in the art upon reading the following detailed description of the presently preferred, but nonetheless illustrative, embodiments when taken in conjunction with the accompanying drawings.

In this respect, before explaining the current embodiments of the sunblock lotion spray booth in detail, it is to be understood that the sunblock lotion spray booth is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the sunblock lotion spray booth.

It is therefore important that the claims be regarded as including such equivalent construction insofar as they do not depart from the spirit and scope of the sunblock lotion spray booth. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
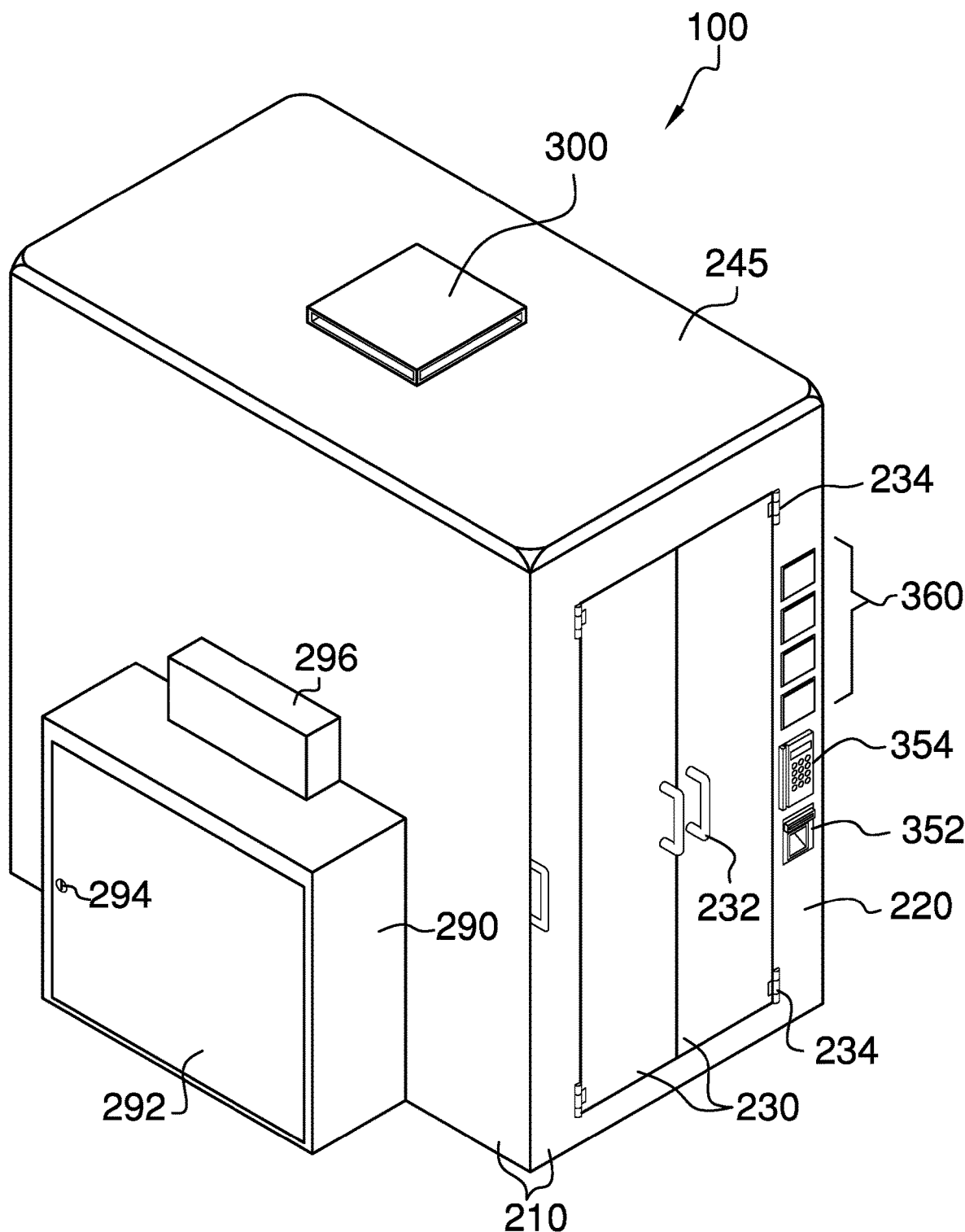
FIG. 1 is a perspective view of an embodiment of the disclosure.
Figure 2:
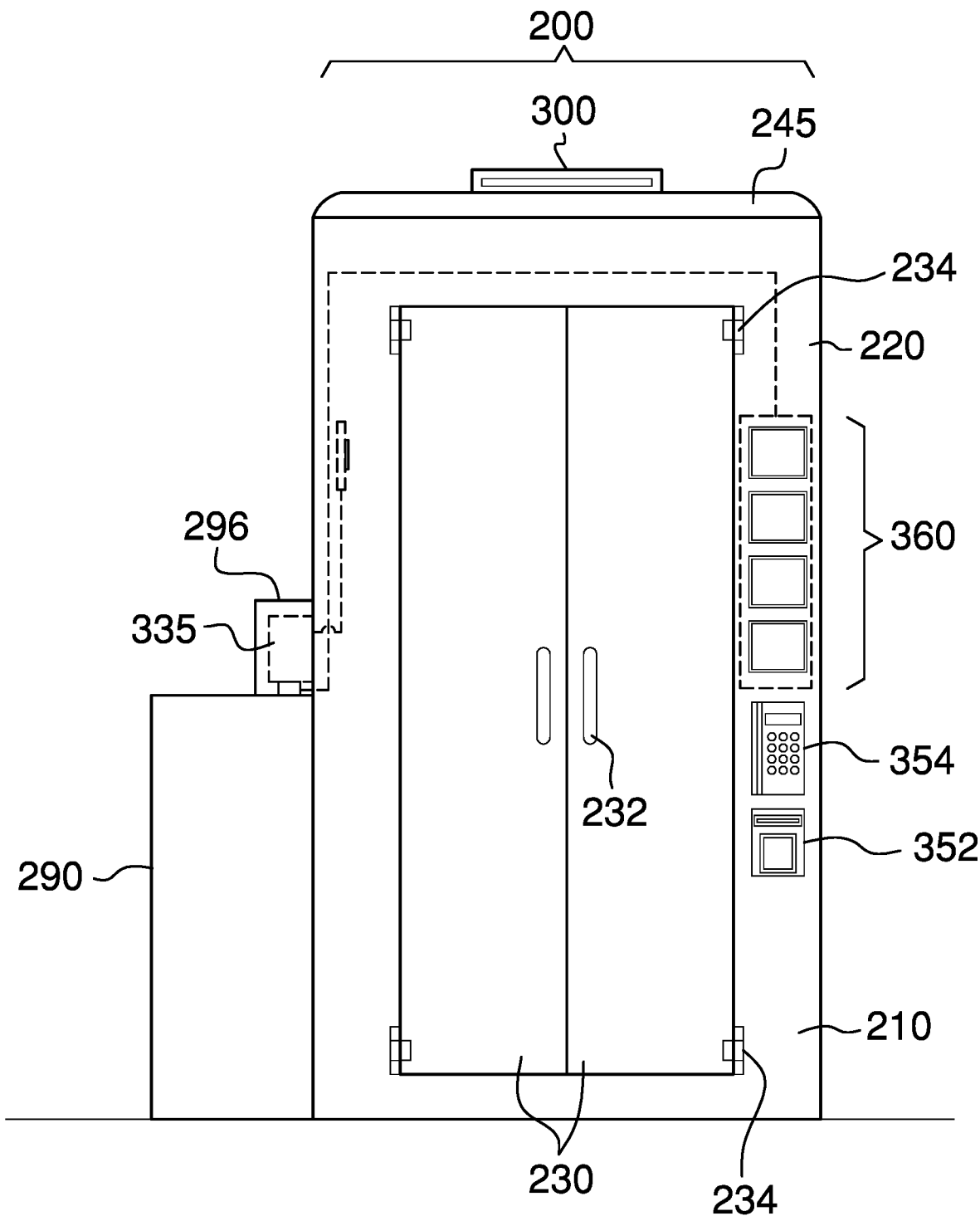
FIG. 2 is a front view of an embodiment of the disclosure.
Figure 3:
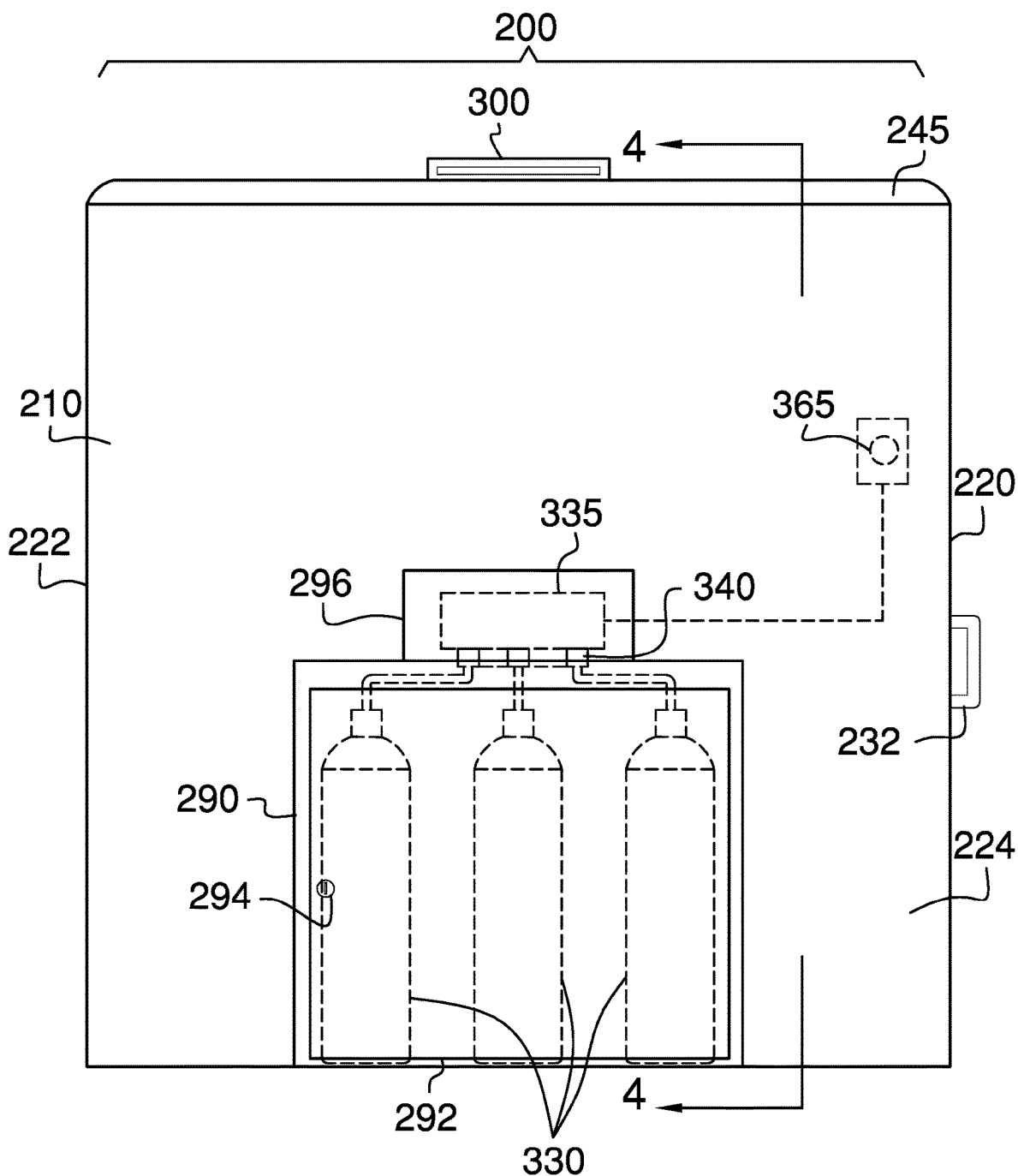
FIG. 3 is a side view of an embodiment of the disclosure.
Figure 4:
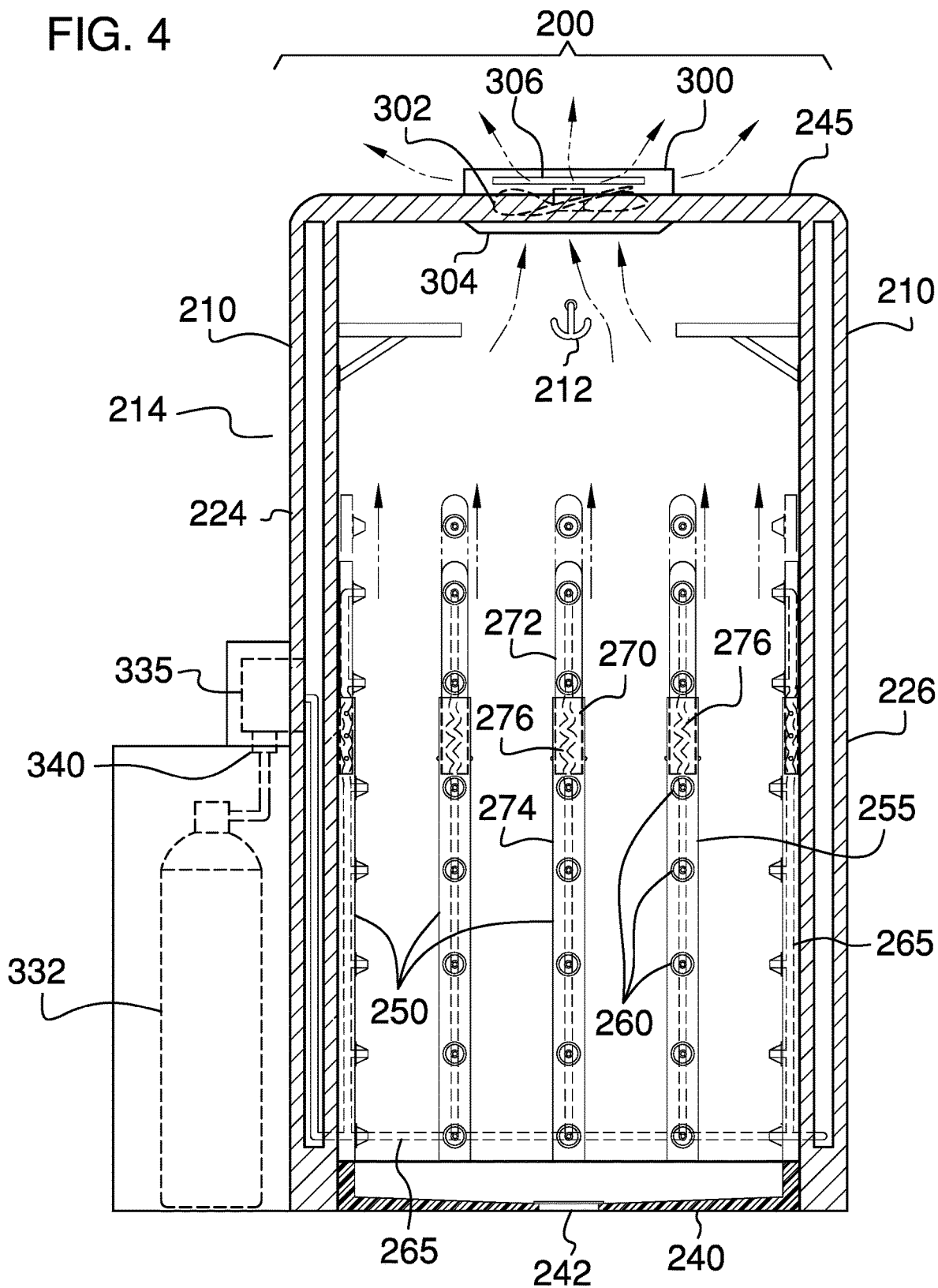
FIG. 4 is a cross-sectional view of an embodiment of the disclosure across 4-4 as shown in FIG. 3.
Figure 5:
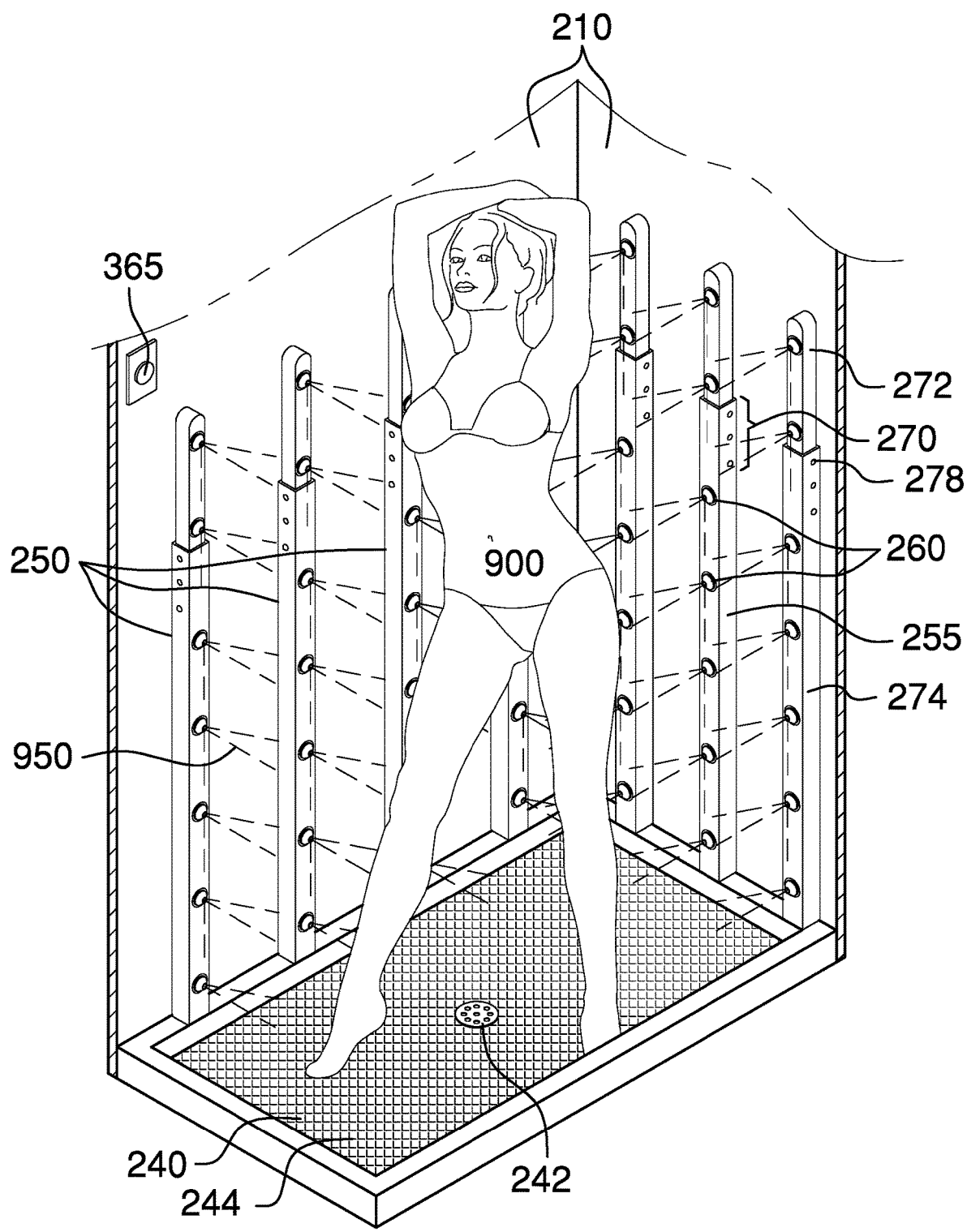
FIG. 5 is a detail view of an embodiment of the disclosure illustrating the tanning products being sprayed onto a user.

Detailed reference will now be made to a first potential embodiment of the disclosure, which is illustrated in FIGS. 1 through 5.

The sunblock lotion spray booth 100 (hereinafter invention) comprises a booth 200, a plurality of spray columns 250, a plurality of canisters 330, a pump 335, a ventilator 300, and one or more payment receiving devices. The booth 200 may be adapted to spray one or more tanning products 950 onto a user 900 via the plurality of spray columns 250 located within the booth 200. As non-limiting examples, the one or more tanning products 950 may be sunblock lotions having different SPF values, bronzers, or combinations thereof. One or more of the plurality of spray columns 250 may be height-adjustable.

The booth 200 may comprise walls 210, a floor 240, and a roof 245. The booth 200 may provide privacy and may prevent wind from blowing the one or more tanning products 950 as they are being sprayed. The walls 210 may house tubing 265 and wiring. One or more doors 230 may be located on a front wall 220. An individual door selected from the one or more doors 230 may be hingedly coupled to the front wall 220 via one or more hinges 234. The individual door may comprise a door handle 232 on the side of the individual door that is opposite the one or more hinges 234. The door handle 232 may cause the individual door to latch or to unlatch such that the individual door may not be opened when latched and the individual door may be opened when unlatched. The door handle 232 may be accessible from either inside of or outside of the booth 200.

The floor 240 may comprise a drain 242 and a non-slip surface 244. The floor 240 may slope downwards from the walls 210 to the drain 242 located at a midpoint of the floor 240 such that the one or more tanning products 950 that are oversprayed are directed towards the drain 242. The non-slip surface 244 may be adapted to prevent the user 900 from slipping and falling.

The roof 245 may cover the booth 200 and may prevent the one or more tanning products 950 from exiting the booth 200 via the top of the booth 200. The roof 245 may house the ventilator 300. The plurality of spray columns 250 may be distributed over the walls 210 of the booth 200 on an interior 212 of the booth 200. An individual spray column 255 selected from the plurality of spray columns 250 may be vertically oriented. The individual spray column 255 may extend from the floor 240 to a height of at least one half of the height of the walls 210 on the interior 212 of the booth 200.

The individual spray column 255 may comprise a plurality of nozzles 260. The plurality of nozzles 260 may convert the one or more tanning products 950 into a mist as the one or more tanning products 950 are forced through the plurality of nozzles 260. The plurality of nozzles 260 may be fluidly connected to each other and to the pump 335 via the tubing 265. The tubing 265 may be vertically oriented within the individual spray column 255 to fluidly connect the plurality of nozzles 260 located on the individual spray column 255. The tubing 265 may be horizontally oriented within the walls 210 of the booth 200 to fluidly connect the bottoms of the plurality of spray columns 250 to each other.

The individual spray column 255 may be adjustable in height. The individual spray column 255 may comprise a height adjuster 270 that allow the height of the top of the plurality of spray columns 250 to be changed.

The height adjuster 270 may comprise an upper spray column 272, a lower spray column 274, a coiled tubing 276, and a position lock 278. The inside diameter of the lower spray column 274 may be at least as large as the outside diameter of the upper spray column 272 such that the upper spray column 272 may slide up and down within the lower spray column 274. The position lock 278 may retain the upper spray column 272 at height until the position lock 278 is disengaged and the upper spray column 272 is allowed to slide up or down until engaging the position lock 278 again. As a non-limiting example, the position lock 278 may comprise a spring-loaded pin in the upper spray column 272 that pushes through one of a plurality of apertures in the lower spray column 274. The coiled tubing 276 within the individual spray column 255 may allow the tubing 265 to change length as the upper spray column 272 moves up or down relative to the lower spray column 274 such that the plurality of nozzles 260 in the upper spray column 272 may be supplied with the one or more tanning products 950.

The plurality of canisters 330 may hold the one or more tanning products 950 that are waiting to be dispensed. Each of the plurality of canisters 330 may hold a different product. As non-limiting examples, a first canister may hold sunblock with an SPF value of 50, a second canister may hold sunblock with an SPF value of 30, and a third canister may hold a bronzer.

The contents of an individual canister 332 selected from the plurality of canisters 330 may flow into the pump 335 via valve 340. If the valve 340 is in an open position then the contents of the individual canister 332 may be pumped from the individual canister 332 to the plurality of nozzles 260 and sprayed. If the valve 340 is in a closed position then the valve 340 prevents the contents of the individual canister 332 from being pumped to the plurality of nozzles 260.

The pump 335 may force the contents of the plurality of canisters 330 to the plurality of nozzles 260 when the pump 335 is energized. As non-limiting examples, the pump 335 may be a piston pump, centrifugal pump, diaphragm pump, or rotary pump. The intake of the pump 335 may be fed with the contents of the plurality of canisters 330 via the valves 340 associated with each of the plurality of canisters 330. The outflow of the pump 335 may be passed through the tubing 265 running through the walls 210 of the booth 200 to the plurality of nozzles 260 on the plurality of spray columns 250.

The plurality of canisters 330 may be enclosed within a canister housing 290 that couples to the walls 210 of the booth 200. The canister housing 290 may be a projection of a left side wall 224, a right side wall 226, or a rear wall 222 on an exterior 214 of the booth 200.

The canister housing 290 may comprise a canister door 292 to provide access to the plurality of canisters 330 from the exterior 214 of the booth 200. The canister door 292 may hingedly couple top the canister housing 290 such that the canister door 292 may be closed to prevent access to the plurality of canisters 330 or opened to permit access to the plurality of canisters 330.

The canister door 292 may comprise a canister door lock 294. The canister door lock 294 may prevent the canister door 292 from being opened when the canister door lock 294 is in a locked state and may allow the canister door 292 to be opened when the canister door lock 294 is in an unlocked state.

The pump 335 may be enclosed within a pump housing 296 that couples to the walls 210 of the booth 200 and couples to the canister housing 290. The pump housing 296 may be a projection of the left side wall 224, the right side wall 226, or the rear wall 222 on the exterior 214 of the booth 200, a projection of the canister housing 290, or a combination thereof.

The ventilator 300 may comprise a motorized fan 302, one or more intake vents 304, and exhaust ports 306. The one or more intake vents 304 may be located inside of the booth 200 and the exhaust ports 306 may be located outside of the booth 200. The motorized fan 302 in the ventilator 300 may turn in a direction that moves air from the one or more intake vents 304 to the exhaust ports 306 when the motorized fan 302 is energized. The ventilator 300 may draw air from within the booth 200 into the one or more intake vents 304 and expel the air outside of the booth 200 via the exhaust ports 306.

The one or more payment receiving devices may be adapted to accept payment from the user 900, accept input from the user 900 via plurality of product selection controls 360, and energize the motorized fan 302, the pump 335, and the valves 340 to dispense the one or more tanning products 950 within the booth 200. The one or more payment receiving devices may be electrically coupled to the pump 335, the valves 340, the motorized fan 302, the plurality of product selection controls 360, and an activation button 365.

The one or more payment receiving devices may comprise a cash payment receiving device 352, a card payment receiving device 354, or both.

The cash payment receiving device 352 may be adapted to accept currency, coins, or both from the user 900. The cash payment receiving device 352 may be adapted to provide change to the user 900 for over payments.

The card payment receiving device 354 may be adapted to accept a debit card, a credit card, or both from the user 900 as a form of payment.

Once payment has been made via the one or more payment receiving devices, the one or more payment receiving devices may be adapted to monitor the plurality of product selection controls 360 located on the exterior 214 of the booth 200 and the activation button 365 located on the interior 212 of the booth 200. When at least one of the plurality of product selection controls 360 have been pressed and the activation button 365 is pressed, the one or more payment receiving devices may energize the motorized fan 302, one or more of the valves 340, and the pump 335 to dispense the one or more tanning products 950. The one or more payment receiving devices may de-energize the pump 335 to terminate the dispensing of the one or more tanning products 950. As a non-limiting example, the one or more payment receiving devices may de-energize the pump 335 after a predetermined time interval has elapsed.

In use, the user 900 may provide a payment at the one or more payment receiving devices and may select the one or more tanning products 950 using the plurality of product selection controls 360. The user 900 may open the one or more doors 230, step inside the booth 200, and close the one or more doors 230. The user 900 may adjust the height adjusters 270 to establish the height of the topmost of the plurality of nozzles 260 on each of the plurality of spray columns 250. The user 900 may disrobe totally or partially if desired and may place their bathing suit or other items on shelves or hooks provided within the booth 200. The user 900 may press the activation button 365 to begin dispensing the one or more tanning products 950.

Responsive to the depression of the activation button 365, the one or more payment receiving devices may energize the valves 340 to release the one or more tanning products 950 selected by the user 900 and may energize the pump 335 to dispense the one or more tanning products 950 via the plurality of nozzles 260. The user 900 may turn slowly within the booth 200 to optimize coverage of their body by the one or more tanning products 950. At the end of the dispense cycle, the one or more payment receiving devices may de-energize the pump 335 and may energize the motorized fan 302 to move air through the booth 200. The user 900 may don their bathing suit and may exit the booth 200 via the one or more doors 230.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" refers to top and "lower" refers to the bottom. As a non-limiting example, the upper end of a vertical shaft is the top end of the vertical shaft.

As used in this disclosure, an "aperture" is an opening in a surface. Aperture may be synonymous with hole, slit, crack, gap, slot, or opening.

As used herein, the words "control" or "controls" are intended to include any device which can cause the completion or interruption of an electrical circuit; non-limiting examples of controls include toggle switches, rocker switches, push button switches, rotary switches, electromechanical relays, solid state relays, touch sensitive interfaces and combinations thereof whether they are normally open, normally closed, momentary contact, latching contact, single pole, multi-pole, single throw, or multi-throw.

As used herein, the words "couple", "couples", "coupled" or "coupling", refer to connecting, either directly or indirectly, and does not necessarily imply a mechanical connection.

As used herein, the word "desired" refers to a specific value or action within a range of supported values or action. A "desired" value or action indicates that a range of values or actions is enabled by the invention and that a user of the invention may select a specific value or action within the supported range of values or action based upon their own personal preference. As a non-limiting example, for a fan that supports operational speed settings of low, medium, or high, a user may select a desired fan speed, meaning that the user may select low, medium, or high speed based upon their needs and preferences at the time of the selection.

As used herein, "energize" and/or "energization" refer to the application of an electrical potential to a system or subsystem.

As used in this disclosure, the word "exterior" is used as a relational term that implies that an object is not located or contained within the boundary of a structure or a space.

As used in this disclosure, a "fan" is a mechanical device with rotating blades that is used to create a flow or current of air.

As used herein, "front" indicates the side of an object that is closest to a forward direction of travel under normal use of the object or the side or part of an object that normally presents itself to view or that is normally used first. "Rear" or "back" refers to the side that is opposite the front.

As used in this disclosure, a "handle" is an object by which a tool, object, or door is held or manipulated with the hand.

As used herein, the terms "height adjustment" or "height adjuster" refer to a mechanism that allows the overall height of an armature or stanchion to change by releasing a locking mechanism, adjusting a position, and re-engaging the locking mechanism. As a non-limiting example, the locking mechanism may comprise a plurality of holes in a first armature and a spring loaded pin on a second armature where the pin passes through one of the holes when the pin and the hole align. As a further non-limiting example, the locating mechanism may comprise a spring-loaded button on an inside armature that pops through one of a plurality of holes in an outside armature and which can be pressed into the hole to release the locking mechanism.

As used in this disclosure, "horizontal" is a directional term that refers to a direction that is perpendicular to the local force of gravity. Unless specifically noted in this disclosure, the horizontal direction is always perpendicular to the vertical direction.

As used in this disclosure, a "housing" is a rigid casing that encloses and protects one or more devices.

As used herein, "inside diameter" or "inner diameter" refers to a measurement made on a hollow object. Specifically, the inside diameter is the distance from one inside wall to the opposite inside wall. If the object is round, then the inside diameter is a true diameter, however the term may also be used in connection with a square object in which case the inside diameter is simply the narrowest inside measurement that passes through the center of the object.

As used in this disclosure, the word "interior" is used as a relational term that implies that an object is located or contained within the boundary of a structure or a space.

As used in this disclosure, a "latch" is a fastening or locking mechanism. The use of the term latch may imply the insertion of an object into a notch or cavity. The act of latching may involve a linear, pivoting, or rotating motion.

As used here, the word "midpoint" refers to a point near the center of an object. An "exact midpoint" refers to a midpoint that is equidistant from edges of the object in at least one direction. Unless otherwise stated, a midpoint is not required to be at the exact center of the object but instead may be within 50% of the distance from the exact midpoint to the farthest edge or farthest corner.

As used here, "non-slip" refers to a property of an object that is makes the object less likely to slide on a flat, wet surface than an object that is not non-slip. Factors that may increase the non-slip characteristics of an object may include the choice of material and the shape of the object. As non-limiting examples, an object with a rubber surface with treads may be considered non-slip.

As used herein, "outside diameter" or "outer diameter" refers to a measurement made on an object. Specifically, the outside diameter is the distance from one point on the outside of the object to a point on the opposite side of the object along a line passing through the center of the object. The term outside diameter is frequently used in conjunction with round objects such as hollow conduits in which case the outside diameter is a true diameter, however the term may also be used in connection with a square object in which case the outside diameter is simply the widest outside measurement that passes through the center of the conduit.

As used in this disclosure, a "pump" is a mechanical or electromechanical device that uses suction or pressure to raise or move fluids, compress fluids, or force a fluid into an inflatable object. As non-limiting examples, fluids may include both liquids, such as water, and gases, such as air.

As used in this disclosure, a "spray" is a plurality of liquid drops projected from a nozzle.

As used in this disclosure, a "spring" is a device that is used to store mechanical energy. This mechanical energy will often be stored by deforming an elastomeric material that is used to make the device, by the application of a torque to a rigid structure, or by a combination thereof. In some embodiments, the rigid structure to which torque is applied may be composed of metal or plastic.

As used in this disclosure, a "tube" is a hollow cylindrical device that is used for transporting liquids and/or gases. In this disclosure, the terms inner diameter and outer diameter are used as they would be used by those skilled in the plumbing arts. The line that connects the center of the first base of the cylinder to the center of the second base of the cylinder and is equidistant from the outer surface of the tube for its entire length is referred to as the centerline of the tube. When two tubes share the same centerline they are said to be aligned. When the centerlines of two tubes are perpendicular to each other, the tubes are said to be perpendicular to each other. As used here, "tubing" refers to a tube that is flexible or resilient.

As used in this disclosure, a "valve" is a device that is used to control the flow of a fluid, either gas or liquid, through a pipe or to control the flow of a fluid into and out of a container. Some valves may have multiple ports and may allow the diverting or mixing of fluids.

As used in this disclosure, "vertical" refers to a direction that is parallel to the local force of gravity. Unless specifically noted in this disclosure, the vertical direction is always perpendicular to horizontal.

Throughout this document references to "wire", "wires", "wired", or "wiring" may describe and/or show a single conductor when, in fact, two conductors may be required to power or control a subsystem; a convention used herein is to not show the common return conductor to which all electrical subsystems are connected—this common return conductor is a continuous electrical path and does not pass through any type of switch or other electrical component other than the possibility of passing through one or more connectors.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A sunblock lotion spray booth comprising:
a booth, a plurality of spray columns, a plurality of canisters, a pump, a ventilator, and one or more payment receiving devices;
wherein the booth is adapted to spray one or more tanning products onto a user via the plurality of spray columns located within the booth;
wherein one or more of the plurality of spray columns are height-adjustable;
wherein an individual spray column selected from the plurality of spray columns is vertically oriented;
wherein the individual spray column is adjustable in height;
wherein the individual spray column comprises a height adjuster that allows the height of the top of the plurality of spray columns to be changed;
wherein the height adjuster comprises an upper spray column, a lower spray column, a coiled tubing, and a position lock;
wherein the inside diameter of the lower spray column is at least as large as the outside diameter of the upper spray column such that the upper spray column slides up and down within the lower spray column;
wherein the position lock retains the upper spray column at height until the position lock is disengaged and the upper spray column is allowed to slide up or down until engaging the position lock again;
wherein the coiled tubing within the individual spray column allows the tubing to change length as the upper spray column moves up or down relative to the lower spray column such that the plurality of nozzles in the upper spray column are supplied with the one or more tanning products.

2. The sunblock lotion spray booth according to claim 1
wherein the booth comprises walls, a floor, and a roof;
wherein the booth provides privacy and prevents wind from blowing the one or more tanning products as they are being sprayed;
wherein the walls house tubing and wiring;
wherein one or more doors are located on a front wall;
wherein an individual door selected from the one or more doors is hingedly coupled to the front wall via one or more hinges;
wherein the individual door comprises a door handle on the side of the individual door that is opposite the one or more hinges;
wherein the door handle causes the individual door to latch or to unlatch such that the individual door does not open when latched and the individual door opens when unlatched;
wherein the door handle is accessible from either inside of or outside of the booth.

3. The sunblock lotion spray booth according to claim 2
wherein the floor comprises a drain and a non-slip surface;
wherein the floor slopes downwards from the walls to the drain located at a midpoint of the floor such that the one or more tanning products that are oversprayed are directed towards the drain;
wherein the non-slip surface is adapted to prevent the user from slipping and falling.

4. The sunblock lotion spray booth according to claim 3
wherein the roof covers the booth and prevents the one or more tanning products from exiting the booth via the top of the booth;
wherein the roof houses the ventilator;
wherein the plurality of spray columns are distributed over the walls of the booth on an interior of the booth;
wherein the individual spray column extends from the floor to a height of at least one half of the height of the walls on the interior of the booth.

5. The sunblock lotion spray booth according to claim 4
wherein the individual spray column comprises a plurality of nozzles;
wherein the plurality of nozzles convert the one or more tanning products into a mist as the one or more tanning products are forced through the plurality of nozzles;
wherein the plurality of nozzles are fluidly connected to each other and to the pump via the tubing;
wherein the tubing is vertically oriented within the individual spray column to fluidly connect the plurality of nozzles located on the individual spray column;
wherein the tubing is horizontally oriented within the walls of the booth to fluidly connect the bottoms of the plurality of spray columns to each other.

6. The sunblock lotion spray booth according to claim 5
wherein the plurality of canisters hold the one or more tanning products that are waiting to be dispensed;
wherein each of the plurality of canisters hold a different product.

7. The sunblock lotion spray booth according to claim 6
wherein the one or more tanning products of an individual canister are selected from the plurality of canisters that flow into the pump via valve;
wherein if the valve is in an open position then the one or more tanning products of the individual canister is pumped from the individual canister to the plurality of nozzles and sprayed;
wherein if the valve is in a closed position then the valve prevents the one or more tanning products of the individual canister from being pumped to the plurality of nozzles.

8. The sunblock lotion spray booth according to claim 7
wherein the pump forces the contents of the plurality of canisters to the plurality of nozzles when the pump is energized;
wherein the intake of the pump is fed with the contents of the plurality of canisters via the valve associated with each of the plurality of canisters;
wherein the outflow of the pump is passed through the tubing running through the walls of the booth to the plurality of nozzles on the plurality of spray columns.

9. The sunblock lotion spray booth according to claim 8
wherein the plurality of canisters are enclosed within a canister housing that couples to the walls of the booth;
wherein the canister housing is a projection of a left side wall, a right side wall, or a rear wall on an exterior of the booth.

10. The sunblock lotion spray booth according to claim 9
wherein the canister housing comprises a canister door to provide access to the plurality of canisters from the exterior of the booth;
wherein the canister door hingedly couples to the canister housing such that the canister door is closed to prevent access to the plurality of canisters or opened to permit access to the plurality of canisters.

11. The sunblock lotion spray booth according to claim 10
wherein the canister door comprises a canister door lock;
wherein the canister door lock prevents the canister door from being opened when the canister door lock is in a locked state and allows the canister door to be opened when the canister door lock is in an unlocked state.

12. The sunblock lotion spray booth according to claim 11
wherein the pump is enclosed within a pump housing that couples to the walls of the booth and couples to the canister housing;
wherein the pump housing is a projection of the left side wall, the right side wall, or the rear wall on the exterior of the booth, a projection of the canister housing, or a combination thereof.

13. The sunblock lotion spray booth according to claim 12
wherein the ventilator comprises a motorized fan, one or more intake vents, and exhaust ports;
wherein the one or more intake vents are located inside of the booth and the exhaust ports are located outside of the booth;
wherein the motorized fan in the ventilator turns in a direction that moves air from the one or more intake vents to the exhaust ports when the motorized fan is energized;
wherein the ventilator draws air from within the booth into the one or more intake vents and expel the air outside of the booth via the exhaust ports.

14. The sunblock lotion spray booth according to claim 13
wherein the one or more payment receiving devices are adapted to accept payment from the user, accept input from the user via plurality of product selection controls, and energize the motorized fan, the pump, and the valves to dispense the one or more tanning products within the booth;
wherein the one or more payment receiving devices are electrically coupled to the pump, the valves, the motorized fan, the plurality of product selection controls, and an activation button;

wherein the one or more payment receiving devices comprise a cash payment receiving device, a card payment receiving device, or both.

15. The sunblock lotion spray booth according to claim 14 wherein the cash payment receiving device is adapted to accept currency, coins, or both from the user;
wherein the cash payment receiving device is adapted to provide change to the user for over payments.

16. The sunblock lotion spray booth according to claim 14 wherein the card payment receiving device is adapted to accept a debit card, a credit card, or both from the user as a form of payment.

17. The sunblock lotion spray booth according to claim 14 wherein once payment has been made via the one or more payment receiving devices, the one or more payment receiving devices are adapted to monitor the plurality of product selection controls located on the exterior of the booth and the activation button located on the interior of the booth;
wherein when at least one of the plurality of product selection controls have been pressed and the activation button is pressed, the one or more payment receiving devices energize the motorized fan, one or more of the valves, and the pump to dispense the one or more tanning products;
wherein the one or more payment receiving devices de-energizes the pump to terminate the dispensing of the one or more tanning products.

18. The sunblock lotion spray booth according to claim 17 wherein the one or more payment receiving devices de-energizes the pump after a predetermined time interval has elapsed.

\* \* \* \* \*